(12) United States Patent
Vega et al.

(10) Patent No.: US 10,380,739 B2
(45) Date of Patent: Aug. 13, 2019

(54) BREAST CANCER DETECTION

(71) Applicant: International Business Machines Corporation, Armonk, NY (US)

(72) Inventors: Juan Manuel A. Vega, Zapopan (MX); Ramón Oswaldo G. Medina, Tecalitlán (MX); Rubén Ruelas-Lepe, Zapopan (MX)

(73) Assignee: International Business Machines Corporation, Armonk, NY (US)

( * ) Notice: Subject to any disclaimer, the term of this patent is extended or adjusted under 35 U.S.C. 154(b) by 91 days.

(21) Appl. No.: 15/677,161

(22) Filed: Aug. 15, 2017

(65) Prior Publication Data

US 2019/0057500 A1 Feb. 21, 2019

(51) Int. Cl.
| | | |
|---|---|---|
| *G06T 7/00* | (2017.01) |
| *G06K 9/40* | (2006.01) |
| *G06K 9/32* | (2006.01) |
| *A61B 5/00* | (2006.01) |
| *G16H 50/20* | (2018.01) |
| *G06T 7/11* | (2017.01) |

(Continued)

(52) U.S. Cl.
CPC .......... *G06T 7/0012* (2013.01); *A61B 5/0091* (2013.01); *A61B 5/6898* (2013.01); *A61B 5/7275* (2013.01); *A61B 5/742* (2013.01); *A61B 5/7485* (2013.01); *G06F 16/5838* (2019.01); *G06K 9/22* (2013.01); *G06K 9/3233* (2013.01); *G06K 9/40* (2013.01); *G06K 9/6218* (2013.01); *G06K 9/6223* (2013.01); *G06T 5/20* (2013.01); *G06T 7/11* (2017.01); *A61B 2576/02* (2013.01); *G06F 19/321* (2013.01); *G06K 2209/053* (2013.01); *G06T 2207/10116* (2013.01); *G06T 2207/30068* (2013.01); *G06T 2207/30096* (2013.01); *G16H 40/63* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 6,137,898 A | 10/2000 | Broussard et al. |
| 7,054,473 B1 | 5/2006 | Roehrig et al. |
| | (Continued) | | |

FOREIGN PATENT DOCUMENTS

| | | | |
|---|---|---|---|
| CN | 104835155 A | 8/2015 |
| CN | 106339591 A | 1/2017 |

OTHER PUBLICATIONS

International Search Report, International Application No. PCT IB2018/055939, dated Dec. 12, 2018, 11 pages.

(Continued)

*Primary Examiner* — Matthew C Bella
*Assistant Examiner* — Brian D Shin
(74) *Attorney, Agent, or Firm* — Scott S. Dobson

(57) ABSTRACT

A hybrid detection model may be used for breast cancer detection. A system can identify a region of interest on a received mammogram. The region of interest may have a particular level of grey at each pixel of the image. A morphological and entropy filter may then each be applied to the region of interest. Based on the filters, the system may generate a hybrid result that is the average of a combination of the two filters. The system may then segment the region of interest using a selected clustering algorithm.

21 Claims, 10 Drawing Sheets

(51) Int. Cl.

| | |
|---|---|
| *G06F 16/583* | (2019.01) |
| *G06K 9/62* | (2006.01) |
| *G06T 5/20* | (2006.01) |
| *G06K 9/22* | (2006.01) |
| G16H 40/63 | (2018.01) |
| G06F 19/00 | (2018.01) |

(56) References Cited

U.S. PATENT DOCUMENTS

| | | | |
|---|---|---|---|
| 8,164,039 B2 | 4/2012 | Bovik et al. | |
| 9,305,204 B2 | 4/2016 | Mukhopadhyay et al. | |
| 2006/0177125 A1* | 8/2006 | Chan | G06K 9/00 382/154 |
| 2012/0075440 A1* | 3/2012 | Ahuja | G06T 7/11 348/61 |
| 2015/0196265 A1 | 7/2015 | Suzuki | |
| 2017/0148166 A1 | 5/2017 | Alpert et al. | |

OTHER PUBLICATIONS

Patel et al., "An Adaptive K-means Clustering Algorithm for Breast Image Segmentation" International Journal of Computer Applications, vol. 10—N.4, Nov. 2010, 4 pages.

Zhang et al., "A Hybrid Image Filtering Method for Computer-Aided Detection of Microcalcification Clusters in Mammograms", Hindawi Publishing Corporation, Journal of Medical Engineering, vol. 2013, Article ID 615254, 9 pages, Accepted Mar. 27, 2013, http://dx.doi.org/10.1155/2013/615254.

Jalalian et al., "Computer-aided detection/diagnosis of breast cancer in mammography and ultrasound: a review", ScienceDirect, Clinical Imaging, vol. 37, Issue 3, 2013, 7 pages. © 2013 Elsevier Inc. http://www.sciencedirect.com/science/article/pii/S0899707112002938.

Tiedeu et al., "Texture-based analysis of clustered microcalcifications detected on mammograms", ScienceDirect, Digital Signal Processing, vol. 22, Issue 1, Jan. 2012, 9 pages. © 2011 Elsevier Inc. http://www.sciencedirect.com/science/article/pii/S1051200411001254?via%3Dihub.

Balakumaran et al., "Detection of Microcalcification in Mammograms Using Wavelet Transform and Fuzzy Shell Clustering", (IJCSIS) International Journal of Computer Science and Information Security, vol. 7, No. 1, 2010, 5 pages.

Philpotts, "Can Computer-aided Detection Be Detrimental to Mammographic Interpretation?" Radiology: vol. 253: No. 1, Oct. 2009, radiology.rsna.org, Copyright RSNA, 2009, 6 pages.

Guardado-Medina et al., "Quality of Microcalcification Segmentation in Mammograms by Clustering Algorithms", International Joint Conference SOCO'13-CISIS'13-ICEUTE'13, Advances in Intelligent Systems and Computing 239, DOI: 10.1007/978-3-319-01854-6_31, Copyright Springer International Publishing Switzerland 2014, 10 pages.

Pasha et al.,"Fuzzy Entropy as Cost Function in Image Processing", Proceedings of the 2nd IMT-GT Regional Conference on Mathematics, Statistics, and Applications, Universiti Sains Malaysia, Penang, Jun. 13-15, 2006, 8 pages.

Pal, "Fuzzy Entropy based feature selection for classification of hyperspectral data", Geospatial World Forum, Jan. 18-21, 2011, Hyderabad, India, Dimensions and Directions of Geospatial Industry, 6 pages.

Tao et al., "Image segmentation by three-level thresholding based on maximum fuzzy entropy and genetic algorithm", ScienceDirect, Pattern Recognition Letters, vol. 24, Issue 16, Dec. 2003, 10 pages. http://www.sciencedirect.com/science/article/pii/S0167865503001661.

Hooda, "On generalized measures of fuzzy entropy", Mathematica Slovaca, vol. 54 (2004), No. 3, 12 pages. © Mathematical Institute of the Slovak Academy of Sciences, 2004.

Parkash et al., "New Generalized Measures of Fuzzy Entropy and Their Properties", Journal of Informatics and Mathematical Sciences, vol. 3 (2011), No. 1, pp. 1-9, © RGN Publications.

Wojtowicz, "An improvement in fuzzy entropy edge detection for X-ray imaging", Schedae Informaticae, vol. 20, 2011, 8 pages. http://www.wuj.pl/UserFiles/File/Schedae%2020/20_08_Wojtowicz.pdf.

Jaffar et al., "Fuzzy Entropy and Morphology Based Fully Automated Segmentation of Lungs From CT Scan Images", International Journal of Innovative Computing, Information and Control, vol. 5, No. 12(B), Dec. 2009, ICIC International Copyright 2009, ISSN 1349-4198, 1 page.

Fernando Soares Servulo de Oliveira et al., "Classification of breast regions as mass and non-mass based on digital mammograms using taxonomic indexes and SVM", ScienceDirect, Computers in Biology and Medicine 57 (2015), 12 pages.

Jen et al., "Automatic detection of abnormal mammograms in mammographic images", ScienceDirect, Expert Systems with Applications, vol. 42, Issue 6, Apr. 15, 2015, Abstract Only, 4 pages. http://www.sciencedirect.com/science/article/pii/S095741741400760X?via%3Dihub.

Dheeba et al., "A Swarm Optimized Neural Network System for Classification of Microcalcification in Mammograms",J Med Syst (2012) 36:3051-3061, DOI 10.1007/s10916-011-9781-3, Copyright Springer Science+Business Media, LLC 2011.

Hornsby et al., "Improved Classification of Mammograms Following Idealized Training", NIH Public Access, Jun. 1, 2014; 3(2), doi:10.1016/j.jarmac.2014.04.009, 16 pages. © 2014 Published by Elsevier Inc on behalf of Society for Applied Research in Memory and Cognition.

Triana et al., "Computer-Aided Detection of Microcalcifications in Digital Mammograms to Support Early Diagnosis of Breast Cancer", International Work-Conference on the Interplay Between Natural and Artificial Computation, IWINAC 2013: Natural and Artificial Models in Computation and Biology, 10 pages. https://rd.springer.com/chapter/10.1007%2F978-3-642-38637-4_30.

Tortajada et al., "Breast peripheral area correction in digital mammograms", ScienceDirect, Computers in Biology and Medicine, vol. 50, 2014, 9 pages. http://www.sciencedirect.com/science/article/pii/S0010482514000730?via%3Dihub.

Vallez et al., "Breast density classification to reduce false positives in CADe systems", ScienceDirect, Computer Methods and Programs in Biomedicine, vol. 113, Issue 2, Feb. 2014, 25 pages. http://www.sciencedirect.com/science/article/pii/S0169260713003441.

Agrawal et al., "Saliency based mass detection from screening mammograms", Signal Processing 99, 2014, Copyright Elsevier B.V., 19 pages. Available Online Dec. 17, 2013.

Pereira et al., "Segmentation and detection of breast cancer in mammograms combining wavelet analysis and genetic algorithm", Computer Methods and Programs in Biomedicine 114 (2014), Accepted Jan. 14, 2014, 14 pages. © 2014 Elsevier Ireland Ltd.

Oliver et al., "Automatic Microcalcification and Cluster Detection for Digital and Digitised Mammograms", Knowledge-Based Systems, vol. 28, Apr. 2012, 21 pages.

Arikidis et al., "Size-adapted microcalcification segmentation in mammography utilizing scale-space signatures", Computerized Medical Imaging and Graphics 34 (2010), Accepted Dec. 9, 2009, © 2009 Elsevier Ltd., 7 pages.

Mohanalin et al., "A novel automatic microcalcification detection technique using Tsallis entropy & a type II fuzzy index", Computers and Mathematics with Applications, 2010, Accepted Aug. 12, 2010, © 2010 Elsevier Ltd., 7 pages.

Papadopoulos et al., "Improvement of microcalcification cluster detection in mammography utilizing image enhancement techniques", Computers in Biology and Medicine, 2008, Accepted Jul. 9, 2008, Copyright 2008 Elsevier Ltd., 11 pages.

National Cancer Institute, NIH, Website Translated, Printed Aug. 1, 2017, 9 pages, https://www.cancergov/espanol.

National Institute of Cancerology, Website Translated, Printed Aug. 1, 2017, 3 pages, http://www.incan.salud.gob.mx/.

(56) References Cited

OTHER PUBLICATIONS

Mell et al., "The NIST Definition of Cloud Computing", Recommendations of the National Institute of Standards and Technology, Sep. 2011, U.S. Department of Commerce, 7 pages.

* cited by examiner

|     |     |     |     |     |     |     |
| --- | --- | --- | --- | --- | --- | --- |
| 123 | 132 | 155 | 174 | 180 | 176 | 159 | 132 |
| 125 | 165 | 189 | 197 | 199 | 198 | 186 | 152 |
| 152 | 190 | 201 | 207 | 206 | 204 | 196 | 171 |
| 166 | 199 | 206 | 206 | 204 | 203 | 199 | 177 |
| 169 | 200 | 205 | 206 | 205 | 206 | 198 | 168 |
| 154 | 187 | 198 | 202 | 199 | 194 | 178 | 136 |
| 125 | 146 | 162 | 168 | 164 | 153 | 132 | 125 |

FIG. 5A

|     |     |     |     |     |     |     |     |
| --- | --- | --- | --- | --- | --- | --- | --- |
| 9   | 18  | 41  | 60  | 66  | 62  | 45  | 17  |
| 11  | 51  | 75  | 83  | 85  | 84  | 72  | 38  |
| 38  | 76  | 87  | 93  | 92  | 90  | 82  | 57  |
| 52  | 85  | 92  | 92  | 90  | 89  | 85  | 63  |
| 55  | 86  | 91  | 92  | 91  | 92  | 84  | 54  |
| 40  | 73  | 84  | 88  | 85  | 80  | 64  | 22  |
| 11  | 32  | 48  | 54  | 50  | 39  | 18  | 7   |

BREAST CANCER DETECTION

BACKGROUND

The present disclosure relates to image processing, and more specifically, to medical image processing for breast cancer detection.

Medical image processing may enable quantitative analysis and visualization of medical images. Various numerical processing techniques may be utilized including spatial filtering, gradient options, unsharp masking and histogram modifications.

Additionally, noise removal techniques may be used in practical application of medical imaging, for example, medical diagnostics. To this end, many noise reducing algorithms have been developed including the Weiner filter, Gaussian filter, median filter, and others.

SUMMARY

Embodiments of the present disclosure may be directed toward a computer-implemented method for a hybrid detection model for use in breast cancer detection. A system may identify a region of interest on a mammogram in response to receiving the mammogram. The mammogram may be a digital image. The region of interest may be described using a level of grey for each point in the region of interest. The system may apply a predetermined morphological filter to each level of grey for each point in the region of interest. The morphological filter may reduce grey levels of the digital image to generate a first set of values. The system may also apply a predetermined entropy filter to each level of grey for each point in the region of interest in the digital image to capture a set of maximum grey values. The maximum grey values may reflect a local maximum relative to other grey values in the digital image. The system may generate a hybrid result that is the average of a combination of the predetermined morphological filter and the predetermined entropy filter. Finally, the system may segment the digital image into potential problem areas by using a selected clustering algorithm with sub-segmentation, using the hybrid result.

Embodiments of the present disclosure may be directed toward a computer system comprising a computer readable storage medium with program instructions stored thereon and one or more processors configured to execute the program instructions to perform a method. The method that may begin when the system identifies a region of interest on a mammogram in response to receiving the mammogram. The mammogram may be a digital image. The region of interest may be described using a level of grey for each point in the region of interest. The system may apply a predetermined morphological filter to each level of grey for each point in the region of interest. The morphological filter may reduce grey levels of the digital image to generate a first set of values. The system may also apply a predetermined entropy filter to each level of grey for each point in the region of interest in the digital image to capture a set of maximum grey values. The maximum grey values may reflect a local maximum relative to other grey values in the digital image. The system may generate a hybrid result that is the average of a combination of the predetermined morphological filter and the predetermined entropy filter. Finally, the system may segment the digital image into potential problem areas by using a selected clustering algorithm with sub-segmentation, using the hybrid result.

Embodiments of the present disclosure may be directed toward a computer program product comprising a computer readable storage medium having program instructions embodied therewith, wherein the computer readable storage medium is not a transitory signal per se, the program instructions executable by a computer processor to cause the processor to perform a method. This method may begin when a system identifies a region of interest on a mammogram in response to receiving the mammogram. The mammogram may be a digital image. The region of interest may be described using a level of grey for each point in the region of interest. The system may apply a predetermined morphological filter to each level of grey for each point in the region of interest. The morphological filter may reduce grey levels of the digital image to generate a first set of values. The system may also apply a predetermined entropy filter to each level of grey for each point in the region of interest in the digital image to capture a set of maximum grey values. The maximum grey values may reflect a local maximum relative to other grey values in the digital image. The system may generate a hybrid result that is the average of a combination of the predetermined morphological filter and the predetermined entropy filter. Finally, the system may segment the digital image into potential problem areas by using a selected clustering algorithm with sub-segmentation, using the hybrid result.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 5A depicts an example gridded greyscale chart of a region of interest, according to embodiments.

FIG. 5B depicts an example gridded greyscale chart resulting from an application of a morphological mathematical filer, according to embodiments.

FIG. 6A depicts an example gridded greyscale chart of a region of interest, according to embodiments.

FIG. 6B depicts an example result of the gridded greyscale chart of FIG. 6B after an application of an entropy filter, according to embodiments.

FIG. 7 depicts an example gridded greyscale chart result of the application of a hybrid filter, according to embodiments.

Figure 1:
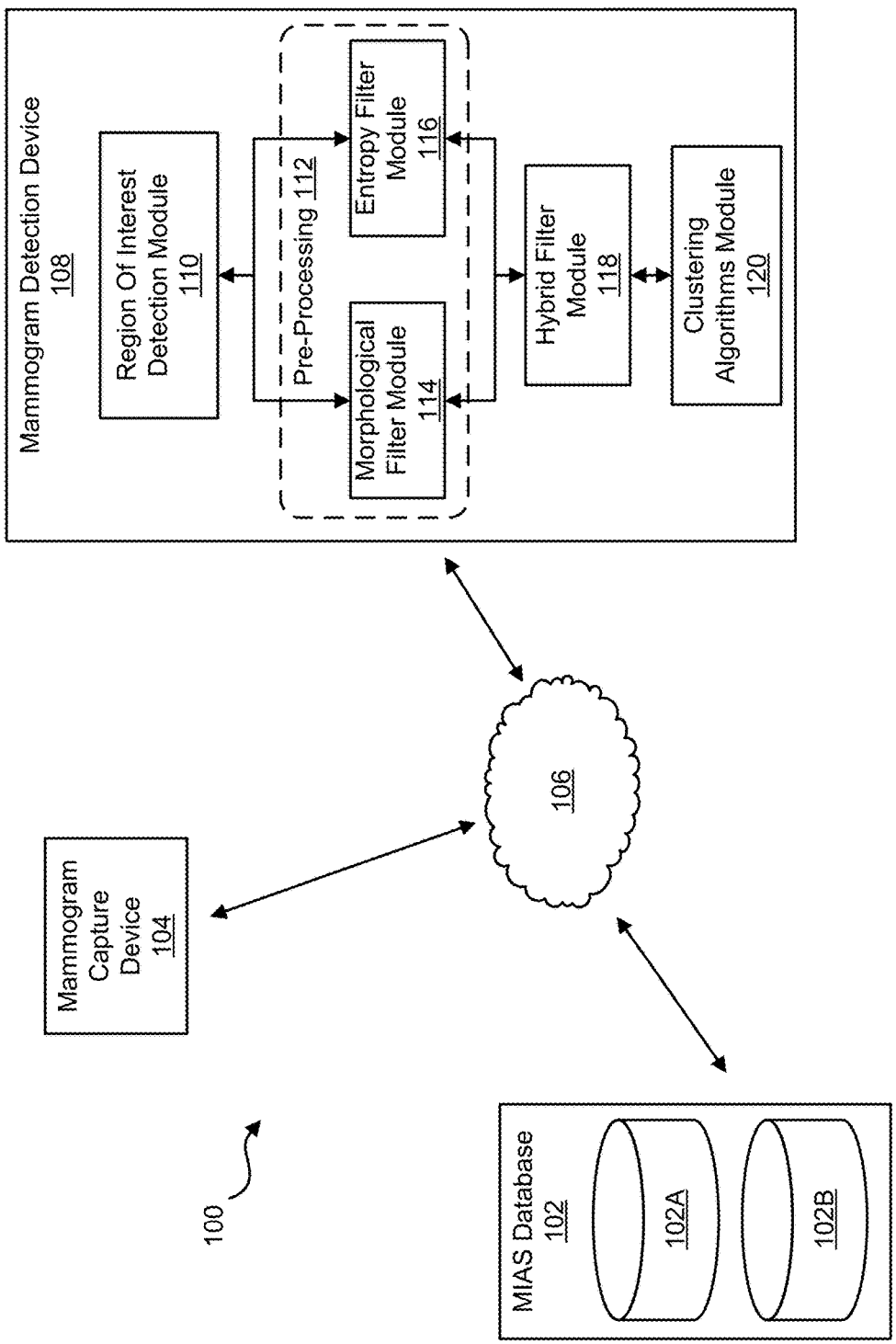
FIG. 1 depicts a system diagram for the identification of microcalcifications in digital mammograms, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to computer-implemented health care, more particular aspects relate to hybrid breast cancer detection. While the present disclosure is not necessarily limited to such applications, various aspects of the disclosure may be appreciated through a discussion of various examples using this context.

The malignancy of breast cancer is unclear and no dominant cause has emerged; however, early detection and treatment may generate a good prognosis for the patient. Currently, X-ray mammography is an important factor in early detection and can greatly reduce the number of deaths caused by breast cancer. This type of mammogram is called a screening mammogram; usually a screening mammogram requires two radiographs or pictures of each breast, as radiographs may enable the detection of tumors that cannot be felt. Mammograms can also find microcalcifications (MCs), or tiny deposits of calcium, which may indicate the presence of breast cancer. As the benefits of early diagnosis are relatively clear, screenings using mammograms may be adopted as frequent and systematic protocol in health assessments of asymptomatic women. This may result in unnecessary biopsies, and include unneeded invasiveness to patients, both physically and psychologically.

Moreover, breast structure between women of differing ages, lifestyles, or other factors, and between two breasts of the same woman, may differ significantly. This may complicate the way clinicians look at and study the existing abnormalities in breast tissue. Additionally, the detection of anomalies through the use of images may also be challenging, as the images often have poor contrast and the images may highlight the differences in breast structure that are considered healthy or normal, rather than drawing attention to problematic abnormalities. Thus, in order to be cautious, radiologists may subject a patient to an invasive diagnosis, like a biopsy.

MCs are small calcium deposits that may accumulate in breast tissue. The MCs usually appear on the mammogram as small bright regions embedded within a heterogenous background. Certain characteristics of MCs, like size, shape, density, distribution pattern, and the number of MCs may be associated with benign or malignant tumors. Malignant MCs may have a diameter less than 0.5 mm, a fine structure, linear branching, and be star shaped.

According to embodiments of the present disclosure, a computer system may receive a mammogram. The mammogram may be received in real-time at a mobile unit located on or near a mammogram capturing device. In other embodiments, the capture of the mammogram may trigger a flow within the same device (e.g., a single unit may both capture and analyze the mammogram).

The system may then identify a region of interest or regions of interest on the mammogram. In embodiments, the region of interest may have a predetermined size, for example a particular number of pixels (e.g., 256×256 pixels). The system may then apply a series of two different filters to the region of interest in order to generate an image (and a corresponding set of values). The series of filters reflects hybrid filter and their application provides for a more accurate identification of pre-cancerous MCs.

In embodiments, the system may first apply a predetermined morphological mathematical filter to grey areas within the region of interest in a black and white digital image. The system may then apply an entropy filter to the image, in order to recapture some of the finer-grain detail that may have been lost in the application of the morphological filter. The results of the two filters may then be averaged to generate a hybrid image and value set. Finally, a clustering algorithm (e.g., k-means or c-means algorithms or other artificial intelligence clustering algorithms) may be applied to highlight potential MCs within the region of interest. In embodiments, the application of a clustering algorithm to the filtered image may be a method of sub-segmenting the image to further define MCs within the region of interest.

FIG. 1 depicts a system diagram 100 for the identification of MCs in digital mammograms, according to embodiments. The system may comprise the elements illustrated and described herein, or more or fewer elements than those depicted in FIG. 1. The system may include a mammogram capture device, 104. In embodiments, this device may be a separate instrument used to capture a mammograph (e.g., a low-ray X ray machine). The images (e.g., digital data) captured by the mammogram capture device 104 may be communicated over a series of one of more networks (e.g., network 106), to a mammogram detection device 108. In some embodiments, the network 106 may be implemented by any number of any suitable communications media (e.g., wide area network (WAN), local area network (LAN), Internet, Intranet, etc.). Alternatively, the mammogram capture device 104 and the mammogram detection device 108 may be local to each other, and may communicate via any appropriate local communication medium (e.g., local area network (LAN), hardwire, wireless link, Intranet, etc.). In some embodiments, the network 106 can be implemented within a cloud computing environment, or using one or more cloud computing services. Consistent with various embodiments, a cloud computing environment may include a network-based, distributed data processing system that provides one or more cloud computing services. Further, a cloud computing environment may include one or more computers, disposed within one or more data centers and configured to share resources over the network 106.

In embodiments, the mammogram capture device 104 may be a part of or coupled with the mammogram detection device 108. In embodiments, both the mammogram capture device 104 and the mammogram detection device 108 may be contained within a mobile computing device. Thus, a physician or other technician could capture a mammogram and analyze it at a patient's bedside, allowing for a reduction in processing time and computational expenditure. In embodiments, this mobile computing device could be a patient bedside unit (e.g., for use in a hospital setting). In embodiments, the mammogram could be captured and processed through an application on a mobile computing device, for example a smart phone, tablet, laptop, or other device.

In embodiments, the mammogram detection device 108 may comprise one or more modules, including, for example, the modules depicted in system 100 of FIG. 1. Program modules may include routines, programs, objects, components, logic, data structures, and so on that perform particular tasks or implement particular abstract data types. In embodiments, each module may comprise one or more executable instructions for implementing the specified logical function(s). For example, the mammogram detection device 108 may include the following modules: a region of interest detection module 110, a set of pre-processing modules 112 including morphological filter module 114 and entropy filter module 116, a hybrid filter module 118 and a clustering algorithms module 120. Each of these modules may be stored locally in the mammogram detection device 108, or they may each be communicatively coupled to the device 108, in order to enable the processes of the modules to be executed remotely (for example, on a remote server).

In embodiments, the devices (e.g., mammogram capture device 104 and the mammogram detection device 108) may communicate over the network 106 with one or more databases, for example a Mammographic Image Analysis Society (MIAS) database 102 depicted at FIG. 1. One or more data repositories, for example, databases 102A and 102B, may contain mammograms and mammographic images from one or more external sources.

Figure 2:
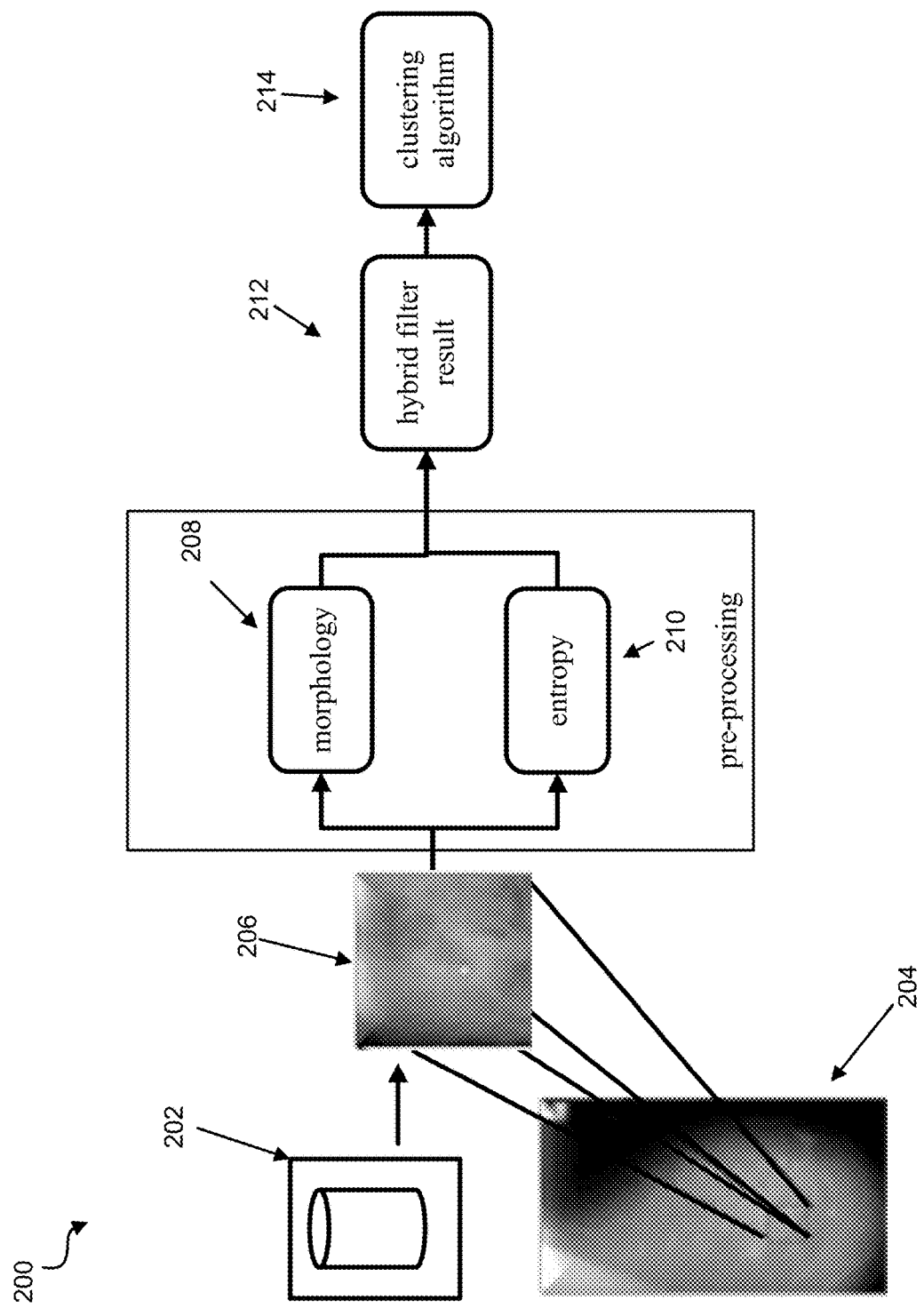
FIG. 2 depicts a visual flow for detection of microcalcifications in digital mammograms, according to embodiments.

FIG. 2 depicts a visual flow of a method 200 for detection of MCs in digital mammograms, according to embodiments. In embodiments, the method 200 may be executed on a single mobile computing device, for example, a smart phone, tablet, or other specialized device. In embodiments, the method 200 may be executed by one or more computer processing circuits on one or more locally or remotely communicating devices.

In embodiments, an image 204, for example, a mammogram as depicted at FIG. 2, may be analyzed, and a particular region of interest (ROI) 206 may be identified for further analysis. In embodiments, the digital image 204 may be accessed from a database, for example an MIAS database 202. In embodiments, mammograms may be automatically uploaded to a shared, public or private, database like an MIAS database 202, in order to be available for analysis or use in research and diagnosis. The MIAS database 202 may also be used in the analyzing of the digital image 204 for an ROI 206. For example, a series of similar digital images could be compared against a new or incoming digital image 204, in order to determine potential abnormalities. In embodiments, the ROI 206 may be identified using a mathematical or intelligence based model, for example, through the use of a trained Convolution Neural Network, through the application of the wavelets method and the use of their Sobelev regularity index, or in another way, as would be evident to one skilled in the art.

In embodiments, an ROI 206 may then be subjected to two different filters based on a morphology method 208 and an entropy method 210. These two mathematical methods may be applied in parallel, as depicted at FIG. 2. As indicated in FIG. 2, subjecting the ROI 206 to the two different filters may be considered a pre-processing stage, as it may occur prior to standard processing procedures. In embodiments, the combination of the application of the two filters, as described herein, may result in a hybrid filter 212. A hybrid filter 212 may provide a combined result of the morphological filter 208 and the entropy filter 210 to the digital image. In embodiments, the application of the classic (or 'non-hybridized') morphological and entropic filters may have differing results.

For example, a morphological filter 208 applied alone to the digital image 204 may attenuate the gray levels of the image, create stronger edges around the object of interest (for example, the MC), and reduce the background noise in the image. The entropy filter 210 when applied on its own may focus on the transitions between shades of grey in the image, which may be recognized by a typical circle that is created through the highlighting of images. The combination of these two filters may result in what is depicted as the hybrid filter result 212. Thus, the hybrid filter result 212 may capitalize on the benefits of each of these mathematical filters, while reducing the negative impacts of each filter. For example, the reduction of noise in the application of the morphology filter 208 can often result in the loss of helpful detail within the digital image 204.

In embodiments, following the application of the hybrid filter result 212, one or more clustering algorithms 214 may be applied to the pixels of the digital image 204 to highlight the identified MCs in the digital image. Some examples of the clustering algorithms 214 include c-means or k-means algorithms. For example, fuzzy c-mean (FCM) or possibilistic fuzzy c-means (PFCM) may be used following the application of the hybrid filter. The use of the hybrid filter prior to the application of one of these basic clustering algorithms may improve effectiveness in the identification of MCs in digital images.

In embodiments, the segmented image could then be displayed for a user (e.g., a healthcare provider, technician, patient, or other appropriate party) on a user interface of a user device. For example, the segmented image could be displayed on a smart phone, tablet, or other personal computing device. The segmented image could also be transmitted to a shared server or local or remote database. The segmented image could also be stored locally on the device, or handled in another manner as appropriate to the context.

Figure 3:
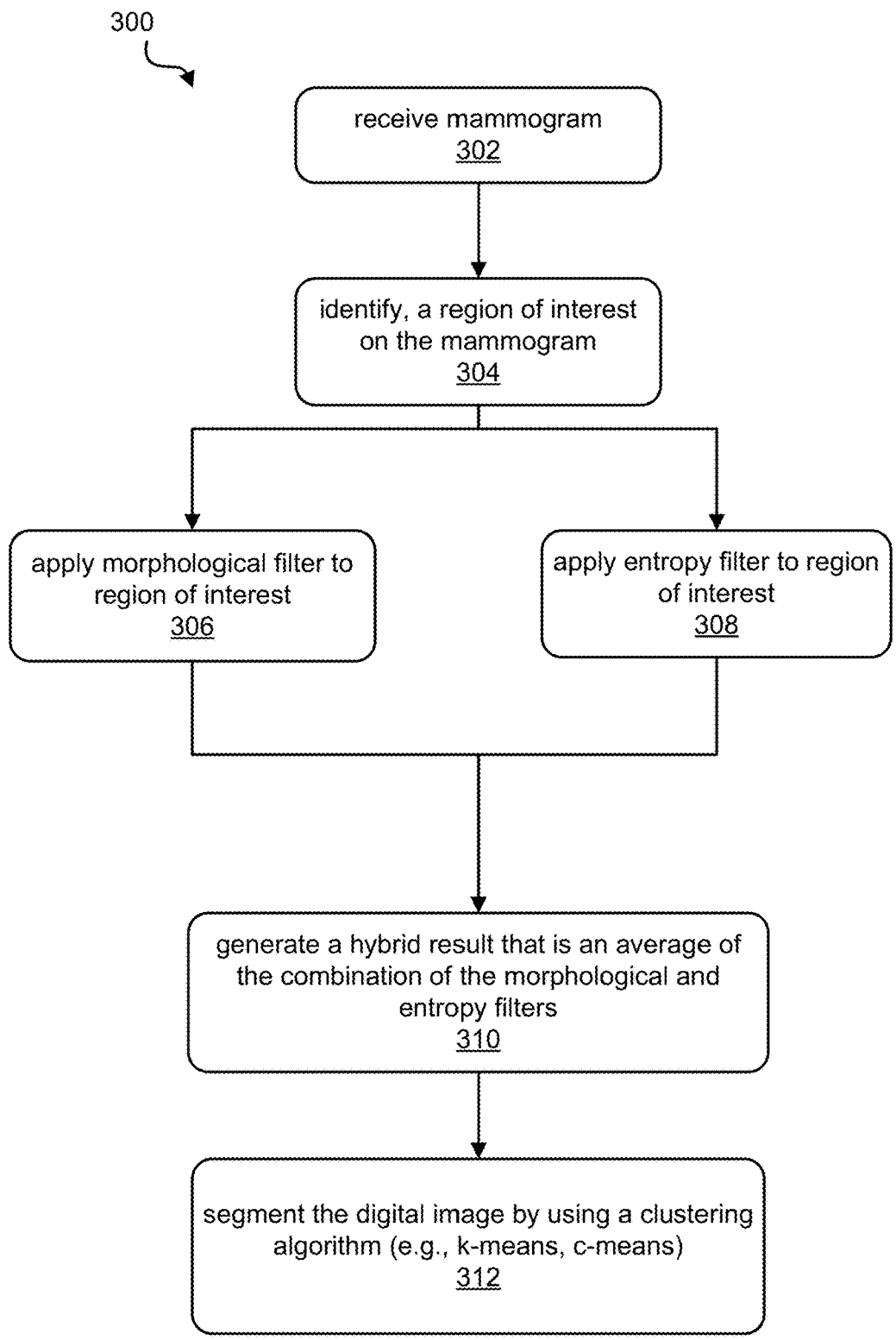
FIG. 3 depicts a flow diagram of a method for detecting microcalcifications in digital mammograms, according to embodiments.

FIG. 3 depicts a flow diagram of a method 300 for detecting MCs in digital mammograms, according to embodiments. In embodiments, the method 300 may be executed by one or more computer processing circuits. The method 300 may begin when a system or device receives a mammogram. In embodiments, the system or device may be a mammogram detection device 108, as described in FIG. 1. As discussed herein, the mammogram detection device and the mammogram capture device (e.g., device 104 in FIG. 1), may be a single device, and thus the identification of a newly captured mammogram by the device would fulfill the receipt of a mammogram step, per 302, and the method may begin.

In embodiments, the system may then identify a region of interest on the mammogram, per 304. According to embodiments, the region of interest may be identified based on data accessed from one or more mammogram repositories, for example, MIAS database 102 depicted at FIG. 1. In embodiments, the system may then apply, to the region of interest a morphological filter, per 306 and an entropy filter, per 308. These filters may be applied in parallel to the region of interest in a digital image (e.g., the mammogram), to generate a hybrid filter result, per 310. The hybrid result may be a combination (e.g., an average) of the transformations of the pixels of the digital image (e.g., the mammogram, which may be a greyscale image), as modified by both the morphological filter and the entropy filter. Finally, the digital image may be segmented by using a clustering algorithm, per 312.

Figure 4B:
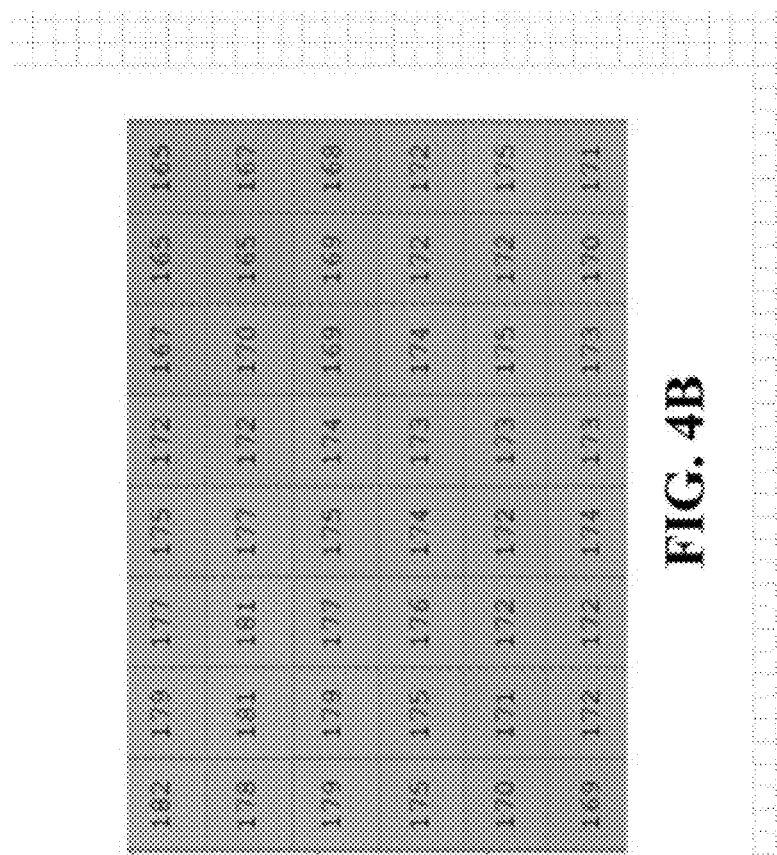
FIG. 4B depicts a gridded greyscale chart of the region of interest, according to embodiments.
Figure 4A:
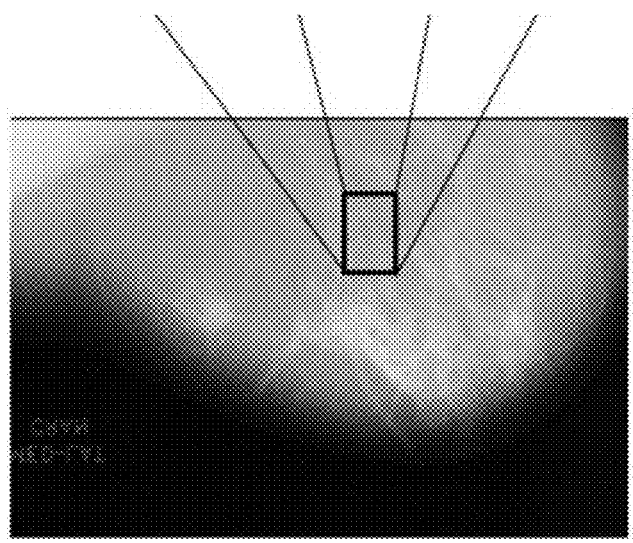
FIG. 4A depicts an image of a mammogram with an identified region of interest, according to embodiments.

FIG. 4A depicts an image of a mammogram with an identified region of interest, according to embodiments. In embodiments, the region of interest depicted at FIG. 4A could be analogous to the RIO 206 in FIG. 2. The region of interest 4A could be sized with 256×256 pixels, and could be a portion of a black and white digital image. The digital image may have been received directly from a mammogram capture device, as described at FIG. 1, or the digital image could be obtained from a database, for example MIAS database 102 of FIG. 1 or 202 of FIG. 2.

FIG. 4B depicts a gridded greyscale chart of the region of interest, according to embodiments. In embodiments, each grid box on the grid of FIG. 4B may represent a single pixel in the region of interest on the mammogram of FIG. 4A. The number contained within each grid box may indicate, numerically, the level of grey contained in each pixel.

FIG. 5A depicts an example gridded greyscale chart of a region of interest, according to embodiments. Similar to FIG. 4B, FIG. 5A depicts a set of image data which numerically indicates a level of grey in each pixel of a region of interest on a digital image, for example, a mammogram. In embodiments, a morphological mathematical filter may be applied to the data contained in the grid, to transform the image to one depicted at FIG. 5B.

FIG. 5B depicts an example gridded greyscale chart resulting from an application of a morphological mathematical filer, according to embodiments. By comparing the grid spaces in FIG. 5A with their analogues in FIG. 5B, it may be noted that the morphological filter results in the loss of grey levels at each pixel. Grey levels both in and around the object may be reduced by this filter. For example, grid space located at the intersection of the first column and the first row changes from 123 down to 9. Similarly, the grid space located at the intersection of the last column and the last row changes from 123 down to 7.

Figures 6A, 6B:
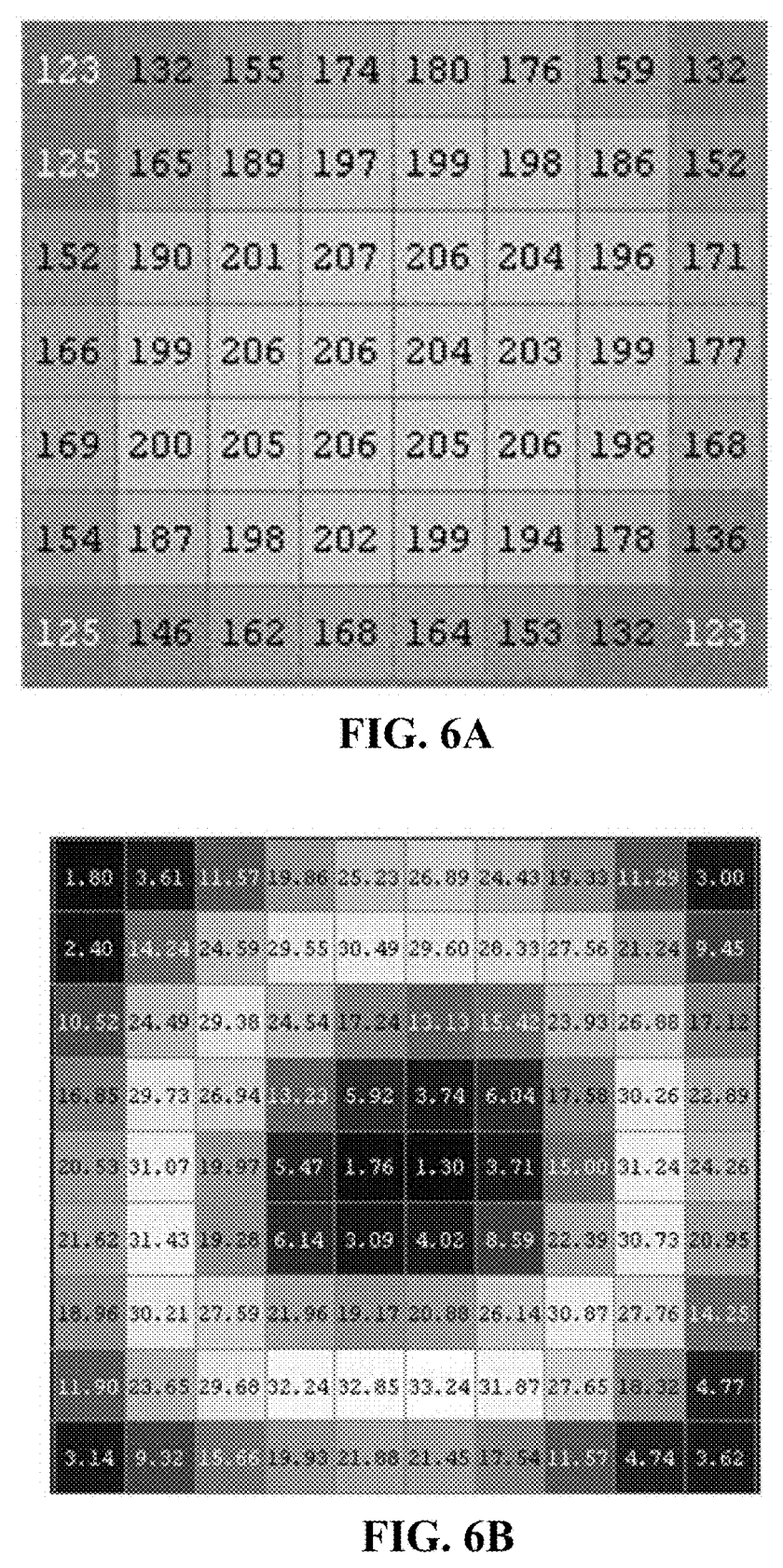

FIG. 6A depicts an example gridded greyscale chart of a region of interest, according to embodiments. Similar to FIG. 5A (and thus FIG. 4B), FIG. 6A depicts a set of image data which numerically indicates a level of grey in each pixel of a region of interest on a digital image, for example, a mammogram. The number values in each grid space may indicate a level of grey in each pixel. A mathematical filter may be applied to the image, for example, an entropy filter as described herein. The result of the application of an example entropy filter to the image is depicted in FIG. 6B.

FIG. 6B depicts an example result of the gridded greyscale chart of FIG. 6B after an application of an entropy filter, according to embodiments. The application of an entropy filter as applied here may increase the size of the image to capture the maximum grey values. In embodiments, this may result in a white ring, which may indicate maximum grey values. In this way, nuanced discrepancies may be highlighted.

Figure 7:
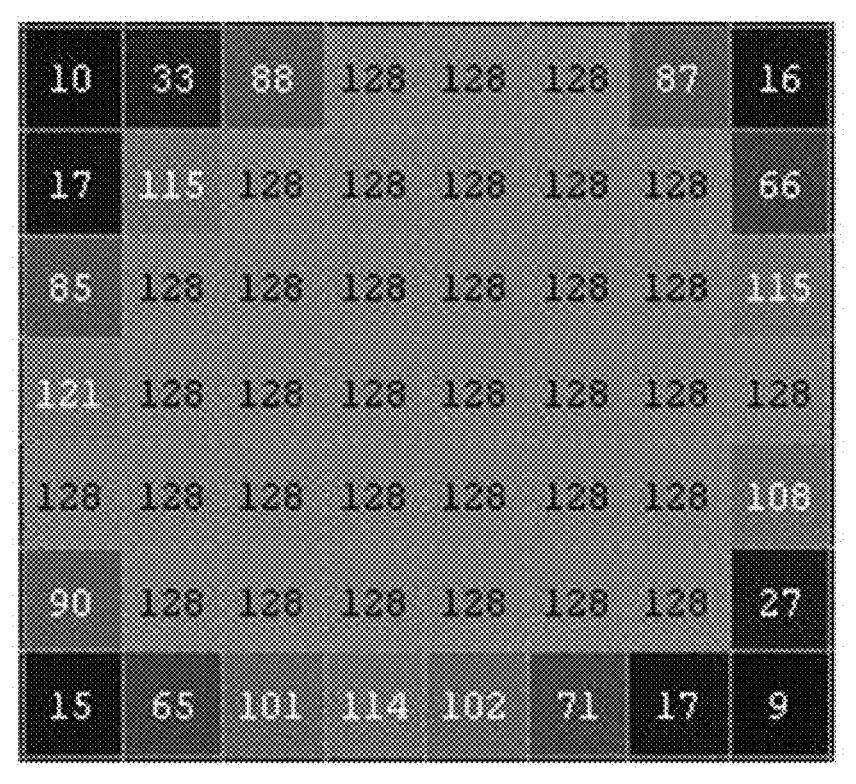

FIG. 7 depicts an example gridded greyscale chart result of the application of a hybrid filter, according to embodiments. The numeric value in each grid space may, like the grid spaces of FIGS. 5 and 6, indicate a greyscale value for each pixel. The values indicated at FIG. 7 may be obtained by averaging the values of the outputs of the morphology filter and the entropy filter for each pixel.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
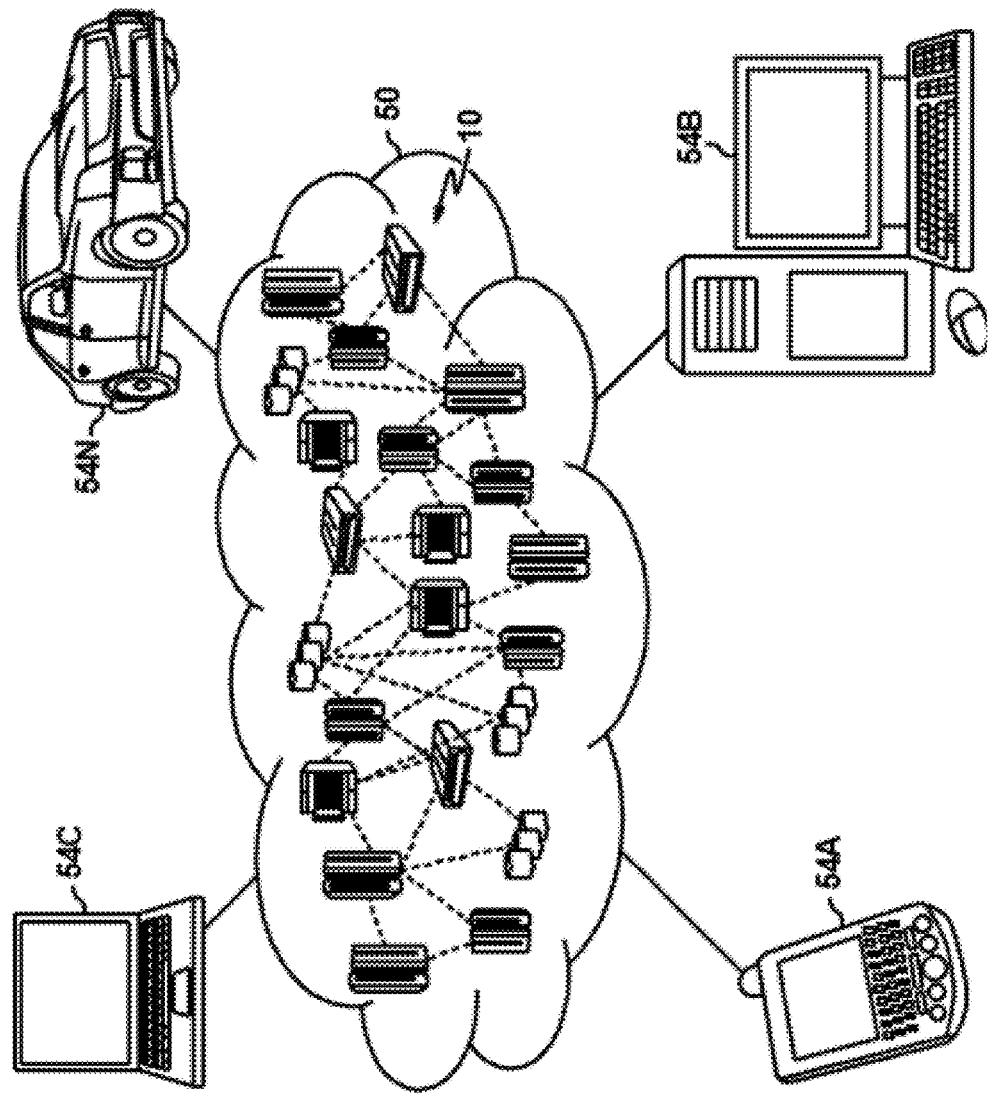
FIG. 8 depicts a cloud computing environment, according to embodiments.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
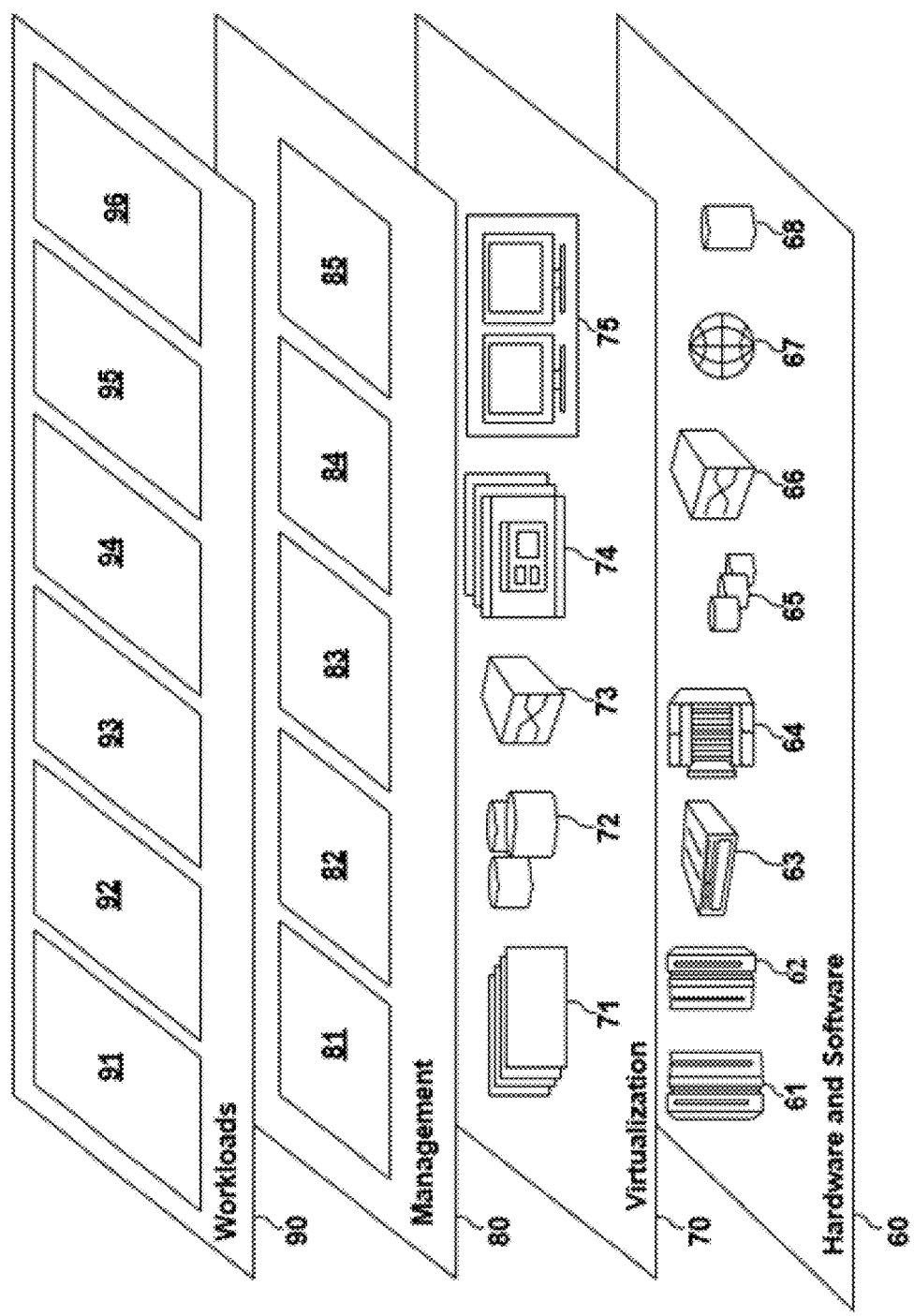
FIG. 9 depicts abstraction model layers, according to embodiments.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and micro calcification detection 96.

Figure 10:
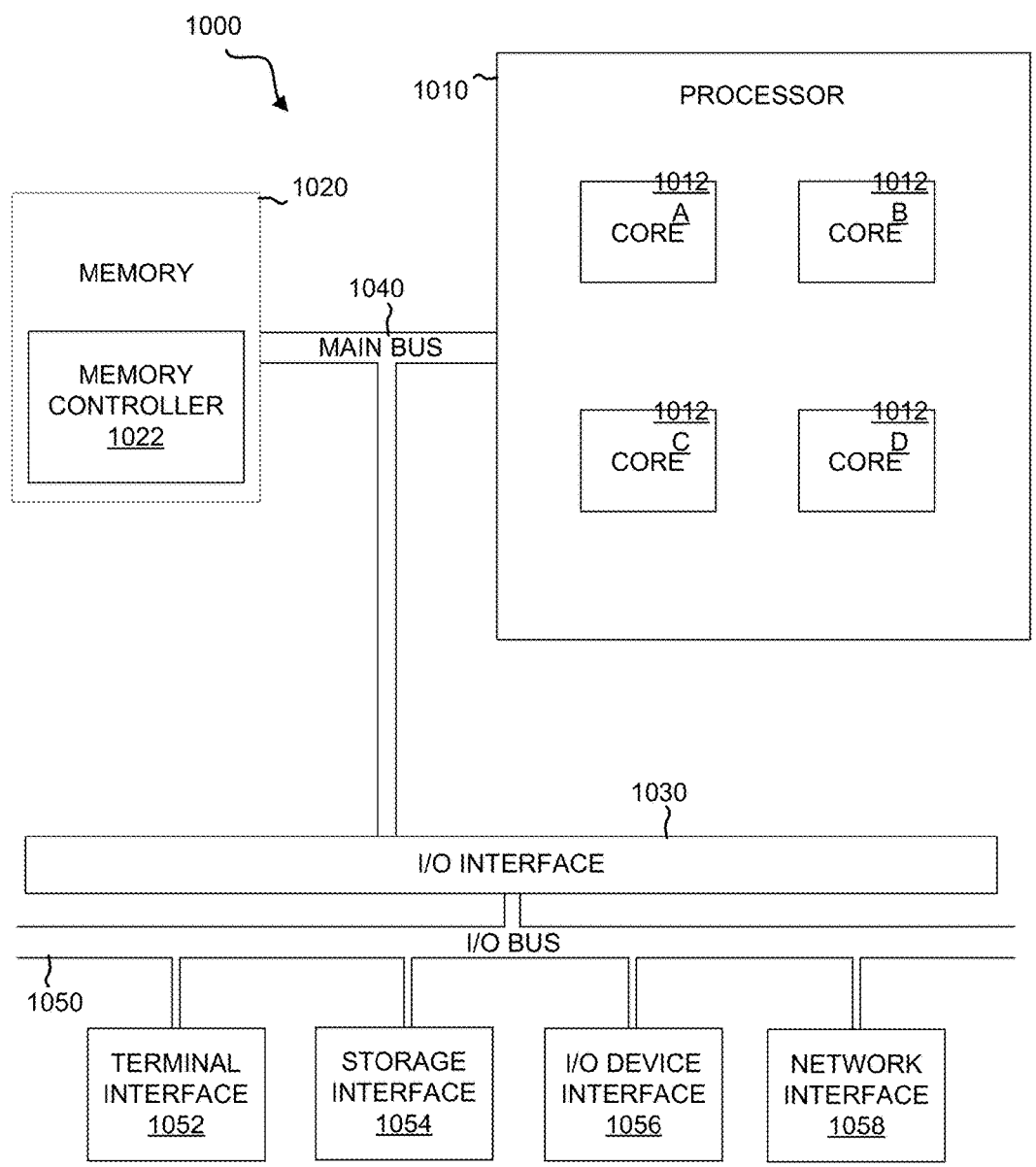
FIG. 10 depicts the representative major components of an example computer system, according to embodiments.

FIG. 10 depicts the representative major components of an example computer system 1000 that may be used, in accordance with embodiments of the present disclosure. It is appreciated that individual components may vary in complexity, number, type, and\or configuration. The particular examples disclosed are for example purposes only and are not necessarily the only such variations. The computer system 1000 may comprise a processor 1010, memory 1020, an input/output interface (herein I/O or I/O interface) 1030, and a main bus 1040. The main bus 1040 may provide communication pathways for the other components of the computer system 1000. In some embodiments, the main bus 1040 may connect to other components such as a specialized digital signal processor (not depicted).

The processor 1010 of the computer system 1000 may be comprised of one or more cores 1012A, 1012B, 1012C, 1012D (collectively 1012). The processor 1010 may additionally include one or more memory buffers or caches (not depicted) that provide temporary storage of instructions and data for the cores 1012. The cores 1012 may perform instructions on input provided from the caches or from the memory 1020 and output the result to caches or the memory. The cores 1012 may be comprised of one or more circuits configured to perform one or more methods consistent with embodiments of the present disclosure. In some embodiments, the computer system 1000 may contain multiple processors 1010. In some embodiments, the computer system 1000 may be a single processor 1010 with a singular core 1012.

The memory 1020 of the computer system 1001 may include a memory controller 1022. In some embodiments, the memory 1020 may comprise a random-access semiconductor memory, storage device, or storage medium (either volatile or non-volatile) for storing data and programs. In some embodiments, the memory may be in the form of modules (e.g., dual in-line memory modules). The memory controller 1022 may communicate with the processor 1010, facilitating storage and retrieval of information in the memory 1020. The memory controller 1022 may communicate with the I/O interface 1030, facilitating storage and retrieval of input or output in the memory 1020.

The I/O interface 1030 may comprise an I/O bus 1050, a terminal interface 1052, a storage interface 1054, an I/O device interface 1056, and a network interface 1058. The I/O interface 1030 may connect the main bus 1040 to the I/O bus 1050. The I/O interface 1030 may direct instructions and data from the processor 1010 and memory 1020 to the various interfaces of the I/O bus 1050. The I/O interface 1030 may also direct instructions and data from the various interfaces of the I/O bus 1050 to the processor 1010 and memory 1020. The various interfaces may include the terminal interface 1052, the storage interface 1054, the I/O device interface 1056, and the network interface 1058. In some embodiments, the various interfaces may include a subset of the aforementioned interfaces (e.g., an embedded computer system in an industrial application may not include the terminal interface 1052 and the storage interface 1054).

Logic modules throughout the computer system 1000—including but not limited to the memory 1020, the processor 1010, and the I/O interface 1030—may communicate failures and changes to one or more components to a hypervisor or operating system (not depicted). The hypervisor or the operating system may allocate the various resources available in the computer system 1000 and track the location of data in memory 1020 and of processes assigned to various cores 1012. In embodiments that combine or rearrange elements, aspects and capabilities of the logic modules may be combined or redistributed. These variations would be apparent to one skilled in the art.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method for a hybrid detection model for use in breast cancer detection, the method comprising:
    identifying, responsive to receipt of a digital image, a region of interest on the digital image, wherein the region of interest is described using a level of grey for each pixel in the region of interest;
    applying, to each level of grey for each pixel in the region of interest in the digital image, a predetermined morphological filter to produce a first output, wherein the morphological filter reduces grey levels of the digital image to generate a first set of values;
    applying, to each level of grey for each pixel in the region of interest in the digital image, a predetermined entropy filter to produce a second output that captures a set of maximum grey values, wherein the maximum grey values reflect a local maximum relative to other grey values in the digital image;
    generating a hybrid result that is a combination of the first output of the predetermined morphological filter and the second output of the predetermined entropy filter; and
    segmenting, using the hybrid result, the digital image into potential microcalcifications by using a selected clustering algorithm with sub-segmentation.

2. The method of claim 1, wherein the selected clustering algorithm includes one of a k-means and c-means.

3. The method of claim 1, further comprising displaying, on a user interface, the segmented digital image.

4. The method of claim 1, further comprising capturing, by a mammogram capture device, the digital image.

5. The method of claim 4, wherein the capturing, identifying, and applying of each of the predetermined morphology filter and the predetermined entropy filter, are performed by a same device, and wherein the device includes the mammogram capture device.

6. The method of claim 5, wherein the device is a smart phone.

7. The method of claim 1, further comprising accessing prior to the identifying, the digital image from a database.

8. The method of claim 1, wherein the digital image is a mammogram.

9. The method of claim 1, wherein generating the hybrid result comprises averaging values of the first output and the second output for each pixel.

10. The method of claim 1, wherein the predetermined morphological filter and the predetermined entropy filter are applied in parallel.

11. A computer system comprising:
    A computer readable storage medium with program instructions stored thereon; and
    one or more processors configured to execute the program instructions to perform a method comprising:
    identifying, responsive to receipt of a digital image, a region of interest on the digital image, wherein the region of interest is described using a level of grey for each pixel in the region of interest;
    applying, to each level of grey for each pixel in the region of interest in the digital image, a predetermined morphological filter to produce a first output, wherein the morphological filter reduces grey levels of the digital image to generate a first set of values;
    applying, to each level of grey for each pixel in the region of interest in the digital image, a predetermined entropy filter to produce a second output that captures a set of maximum grey values, wherein the maximum grey values reflect a local maximum relative to other grey values in the digital image;
    generating a hybrid result that is a combination of the first output of the predetermined morphological filter and the second output of the predetermined entropy filter; and
    segmenting, using the hybrid result, the digital image into potential microcalcifications by using a selected clustering algorithm with sub-segmentation.

12. The system of claim 11, wherein the selected clustering algorithm includes one of a k-means and c-means.

13. The system of claim 11, wherein the method further comprises displaying, on a user interface, the segmented digital image.

14. The system of claim 11, wherein the method further comprises capturing, by a mammogram capture device, the digital image.

15. The system of claim 11, wherein the system further comprises a mammogram capture device.

16. The system of claim 11, wherein the method further comprises accessing, prior to the identifying, the digital image from a database.

17. The system of claim 11, wherein the digital image is a mammogram.

18. A computer program product comprising a computer readable storage medium having program instructions embodied therewith, wherein the computer readable storage medium is not a transitory signal per se, the program instructions executable by a computer processor to cause the processor to perform a method comprising:
    identifying, responsive to receipt of a digital image, a region of interest on the digital image, wherein the region of interest is described using a level of grey for each pixel in the region of interest;
    applying, to each level of grey for each pixel in the region of interest in the digital image, a predetermined morphological filter to produce a first output, wherein the morphological filter reduces grey levels of the digital image to generate a first set of values;

applying, to each level of grey for each pixel in the region of interest in the digital image, a predetermined entropy filter to produce a second output that captures a set of maximum grey values, wherein the maximum grey values reflect a local maximum relative to other grey values in the digital image;

generating a hybrid result that is a combination of the first output of the predetermined morphological filter and the second output of the predetermined entropy filter; and segmenting, using the hybrid result, the digital image into potential microcalcifications by using a selected clustering algorithm with sub-segmentation.

19. The computer program product of claim 18, wherein the selected clustering algorithm includes one of a k-means and c-means.

20. The computer program product of claim 18, wherein the method further comprises accessing, prior to the identifying, the digital image from a database.

21. The computer program product of claim 18, wherein the digital image is a mammogram.

\* \* \* \* \*